US00PP21745P3

(12) United States Plant Patent
Nagamori

(10) Patent No.: US PP21,745 P3
(45) Date of Patent: Mar. 1, 2011

(54) ***CYMBALARIA* PLANT NAMED 'SNOW WAVE'**

(50) Latin Name: *Cymbalaria muralis*
Varietal Denomination: Snow Wave

(76) Inventor: Masao Nagamori, Chiba-ken (JP)

( * ) Notice: Subject to any disclaimer, the term of this patent is extended or adjusted under 35 U.S.C. 154(b) by 63 days.

(21) Appl. No.: 12/462,003

(22) Filed: Jul. 27, 2009

(65) Prior Publication Data

US 2010/0175159 P1 Jul. 8, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Wendy Haas
(74) *Attorney, Agent, or Firm*—Klarquist Sparkman, LLP

(57) ABSTRACT

A new and distinct form of *Cymbalaria muralis* plant characterized by its unique, broadly cream-edged foliage and white flowers.

1 Drawing Sheet

Botanical denomination: *Cymbalaria muralis* 'Albiflora'. Variety designation: 'Snow Wave'.

BACKGROUND OF THE INVENTION

The present invention relates to a new and distinct cultivar of *Cymbalaria muralis* 'Albiflora', given the name, 'Snow Wave'. *Cymbalaria* is in the family Scrophulariaceae. This plant was found as a branch mutation in a nursery in Japan. *Cymbalaria* 'Snow Wave' differs from its parent plant in being having broad creamy white leaf margins rather than all green leaves.

*Cymbalaria* 'Snow Wave' is unique. There are no similar plants in the commercial market known to the inventor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old *Cymbalaria* 'Snow Wave' growing in a container in spring in Japan.

FIG. 2 shows a close up.

DETAILED PLANT DESCRIPTION

The following is a detailed description of the new *Cymbalaria* cultivar based on observations of three-month-old specimen grown in a cool greenhouse in Canby, Oreg. The color descriptions are all based on The Royal Horticultural Society Colour Chart, 1998 edition.

Plant:

*Form.*—Trailing, herbaceous perennial.
*Cold hardiness.*—USDA Zone 3-9.
*Size.*—Grows to 30 cm wide and 11 cm high.

*Vigor.*—Excellent.
*Stem.*—Slender, 21 cm long and 1 mm wide, Green 146B, with internodes to 3.5 cm long, glabrous.
*Roots.*—White 155B, fibrous, plants root easily from stem cuttings.

Leaf:

*Type.*—Simple.
*Arrangement.*—Alternate.
*Shape.*—Reniform to orbicular, shallowly 5 to 7 lobed.
*Venation.*—Pinnate.
*Margins.*—Entire.
*Apex.*—Mucronulate.
*Base.*—Cordate.
*Blade size.*—Grows to 11 mm long and 14 mm wide.
*Surface texture.*—Glabrous on both sides.
*Petiole description.*—Grows to 15 mm long, glabrous, Yellow Green 138C.
*Leaf color.*—Topside center is Greyed Green 191A lightening to 191C in areas near the edge closest to the leaf margin, leaf margins are Yellow Green 150D; bottom side center is Greyed Green 191A with margins Yellow Green 154C.

Inflorescence:

*Type.*—Solitary, axillary.
*Pedicel.*—15 mm long, Yellow Green 146B.
*Bloom period.*—June to September in Canby, Oreg.

Flower bud:

*Size.*—6 mm long and 3 mm wide at the widest point prior to opening.
*Description.*—Tubular, spurred.
*Surface texture.*—Glabrous.
*Color.*—White 155A.

Flower:

*Type.*—Zygomorphic.
*Shape.*—Bilabiate.
*Corolla description.*—10 mm long and spreads to 8 mm wide, 5 lobes, spur 1.5 mm long, tube 3.5 mm long and 2 mm wide, 2 upper lobes together, 4 mm long and 1.5 mm wide, obovate, entire, obtuse; three lower lobes from a protruding 2 parted pouch-like throat (2 mm deep), lobes spreading 8 mm wide, each lobe 2.5 mm long and less than 2 mm wide, White 155D with throat Yellow Orange 15A; glabrous outside, pubescent along throat inside.

*Calyx description.*—5 lobed, acute, entire, 2 mm long and 2 mm wide, glabrous inside and out, White 155A.

*Pistil description.*—1, 3 mm long, ovary 1 mm long, Yellow Green 145B, style and stigma 2 mm long, White 155D.

*Stamen description.*—4, filaments 4.5 mm long and White 155D, anthers undehisced Yellow White 158D, pollen Yellow White 158B.

*Fragrance.*—None.

*Lastingness.*—A flower lasts about 5 days on the plant.

Fruit: Capsule, none seen.

Seed: None seen.

Pests and diseases: *Cymbalaria* are known to have infrequent pest or disease problems. The new cultivar has no known resistances.

I claim :

1. A new and distinct form of *Cymbalaria* plant substantially as shown and described.

* * * * *

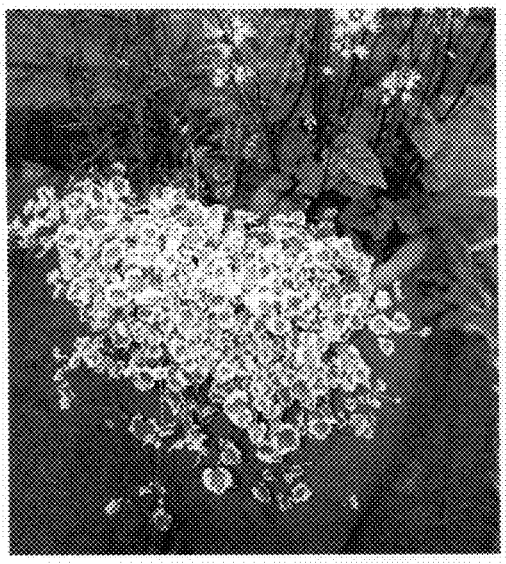
Figure 1 above, figure 2 below
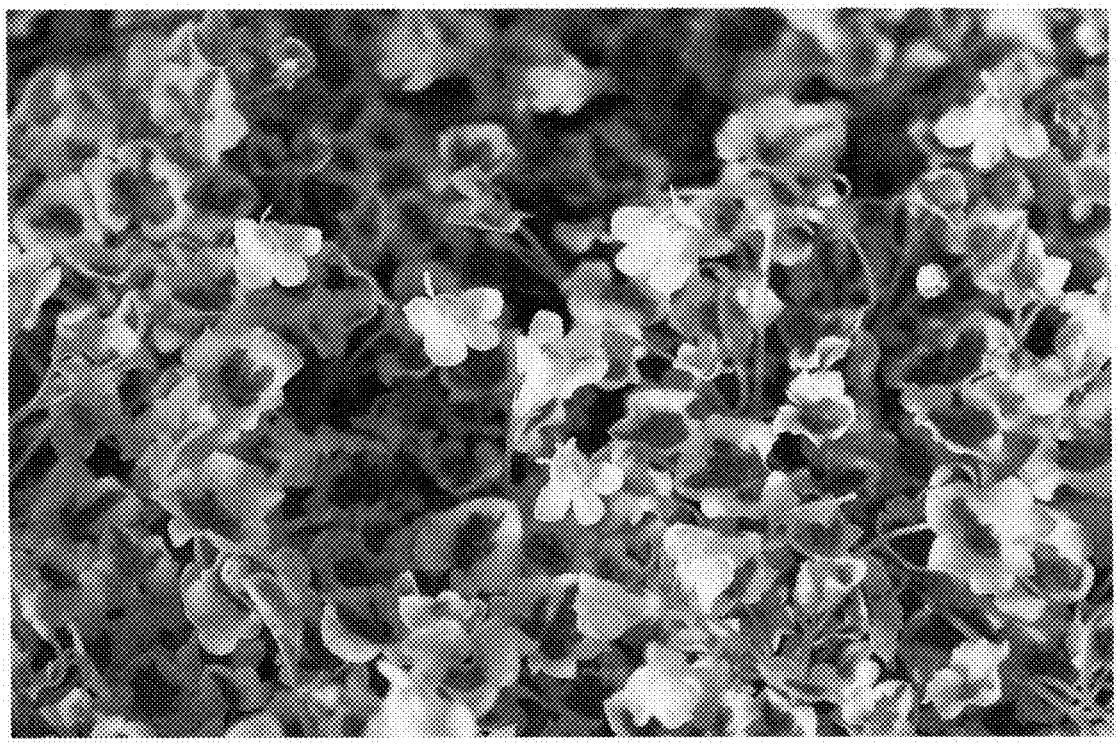

UNITED STATES PATENT AND TRADEMARK OFFICE

CERTIFICATE OF CORRECTION

PATENT NO. : PP21,745 P3
APPLICATION NO. : 12/462003
DATED : March 1, 2011
INVENTOR(S) : Masao Nagamori It is certified that error appears in the above-identified patent and that said Letters Patent is hereby corrected as shown below:

On the Cover Page:

The Foreign Application Priority Data should be added as follows:

--January 3, 2009 Japan 23799--

Signed and Sealed this
Thirtieth Day of August, 2011

David J. Kappos

David J. Kappos
*Director of the United States Patent and Trademark Office*